United States Patent [19]

Gandolfi et al.

[11] Patent Number: 5,047,414
[45] Date of Patent: Sep. 10, 1991

[54] 2-(AMINOALKYLTHIO)METHYL-1,4-DIHYDROPYRIDINE, A METHOD FOR THE PREPARATION THEREOF AND PHARMACEUTICAL COMPOSITIONS CONTAINING THEM

[75] Inventors: Carmelo A. Gandolfi; Marco Frigerio; Silvano Spinelli; Odoardo Tofanetti; Sergio Tognella, all of Milan, Italy

[73] Assignee: Boehringer Biochemia Robin S.p.A., Milan, Italy

[21] Appl. No.: 638,131

[22] Filed: Dec. 21, 1990

Related U.S. Application Data

[63] Continuation of Ser. No. 299,992, filed as PCT EP 87/00335 on Jun. 25, 1987, published as WO 88/00187 on Jan. 14, 1988 abandoned.

[30] Foreign Application Priority Data

Jun. 27, 1986 [IT] Italy ............................... 20965A/86

[51] Int. Cl.$^5$ ................. A61K 31/435; A61K 31/335; A61K 31/40; C07D 211/68; C07D 211/80; C07D 213/02
[52] U.S. Cl. .................................. 514/338; 514/318; 514/332; 514/333; 514/334; 514/335; 514/336; 514/337; 514/343; 514/344; 514/346; 514/349; 514/350; 514/352; 514/356; 546/194; 546/255; 546/256; 546/257; 546/269; 546/270; 546/281; 546/283; 546/284; 546/286; 546/287; 546/309; 546/310; 546/316; 546/318; 546/321; 546/322
[58] Field of Search ............... 546/194, 255, 256, 257, 546/269, 270, 281, 283, 284, 286, 287, 307, 310, 316; 546/318, 321, 322, 318, 322, 333, 334, 335, 336, 337, 338, 343, 344, 346, 349, 350, 352, 356

[56] References Cited

FOREIGN PATENT DOCUMENTS 0060674 9/1982 European Pat. Off. ............ 546/194
0095450 11/1983 European Pat. Off. ............ 546/194
0106462 4/1984 European Pat. Off. ............ 546/194
0116769 8/1984 European Pat. Off. ............ 546/194
0119050 9/1984 European Pat. Off. ............ 546/194
172029 2/1986 European Pat. Off. ............ 546/194
0172029 2/1986 European Pat. Off. ............ 546/194
8700836 2/1987 World Int. Prop. O. .......... 546/194

Primary Examiner—Johann Richter
Attorney, Agent, or Firm—Armstrong, Nikaido, Marmelstein, Kubovcik & Murray

[57] ABSTRACT

Compounds of formula I, and pharmaceutical compositions containing compounds of formula I

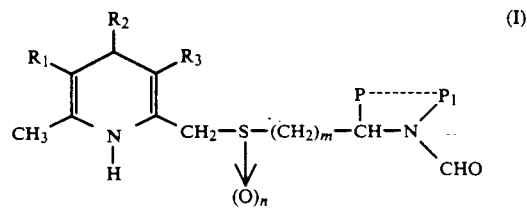

wherein:
$R_1$ is:
(a) $COCH_3$, $COC_6H_5$, CN or $NO_2$;
(b) COORa wherein Ra is hydrogen, or optionally substituted $C_1$-$C_6$ straight or branched alkyl;
$R_2$ is optionally substituted phenyl; pentafluorophenyl; α- or β-naphthyl; a five- or six-membered heterocyclic ring; α-benzo[2,3-b]-1,4-dioxan-α-yl; or α-benzofuroxanyl;
$R_3$ is COORa;
P is hydrogen, —$(CH_2)_p$—W, or $C_1$-$C_8$ linear or branched alkyl;
N—$P_1$ is the residue of a primary or secondary amino group wherein $P_1$ is hydrogen, $C_1$-$C_6$ lower linear or branched alkyl group, or —$(CH_2)_p$—W; and P, taken together with $P_1$ and the nitrogen atom to which $P_1$ is linked, may form a pyrrolidine or a piperidine ring; W is hydroxymethyl, formyloxymethyl, $CO_2R$ wherein R is hydrogen or $C_1$-$C_4$ lower alkyl, CN, saturated or unsaturated heterocyclic ring, $C_3$-$C_7$ cycloalkyl ring, or optionally substituted phenyl;
m is an integer from 1 to 3;
n is zero or an integer from 1 to 2;
p is zero or an integer from 1 to 3.

The compounds of formula (I) and compositions containing them are effective in anti-hypertensive therapy.

10 Claims, No Drawings

2-(AMINOALKYLTHIO)METHYL-1,4-DIHYDROPYRIDINE, A METHOD FOR THE PREPARATION THEREOF AND PHARMACEUTICAL COMPOSITIONS CONTAINING THEM

This application is a continuation of application Ser. No. 299,992 filed as PCT EP87/00335 on Jun. 25, 1987, published as WO88/00187 on Jan. 14, 1988, now abandoned.

Object of the present invention are 2-(formylaminoalkylthio)-methyl-1,4-dihydropyridine, a method for the preparation thereof and pharmaceutical compositions containing them.

The compounds object of the present invention have the following general formula I

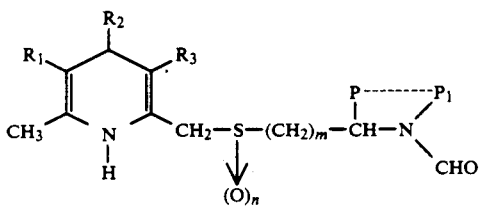

wherein:
$R_1$ represents:
- a $COCH_3$, $COC_6H_5$, CN or $NO_2$ group;
- a $COORa$ group, wherein Ra represent hydrogen, $C_1$-$C_6$ straight or branched alkyl, optionally bearing one or more $C_1$-$C_6$ alkoxy groups and/or secondary amino groups of formula $-NR_4R_5$ wherein $R_4$ and $R_5$, that may be the same or different, represent $C_1$-$C_6$ alkyl, phenyl, benzyl or taken, together with the nitrogen atom, form a five or six membered ring optionally containing other atoms;

$R_2$ is a phenyl ring unsubstituted or substituted with one or more $C_1$-$C_6$ alkyl, halogen, nitro, cyano, $C_1$-$C_6$ alkoxycarbonyl, $C_1$-$C_6$ alkylthio, $C_1$-$C_6$ alkylsulfynyl; pentafluorophenyl; α- or β-naphthyl; a five- or six-membered heterocyclic ring; α-benzo[2.3-b]-1.4-dioxan-α-yl; α-benzofuroxanyl;

$R_3$ represents a $COORa$ group wherein Ra is as above defined;

P is selected from the group consisting of hydrogen, $-(CH_2)_p$-W and $C_1$-$C_8$ linear or branched alkyl;

N-$P_1$ is the residue of a primary or secondary amino group wherein $P_1$ is selected from the group consisting of hydrogen, $C_1$-$C_6$ lower linear or branched alkyl group and $-(CH_2)p$-W;

P, taken together with $P_1$ and the nitrogen atom to which $P_1$ is linked, may form a pyrrolidine or a piperidine ring;

W is selected from the group consisting of hydroxymethyl, formyloxymethyl, $CO_2R$ wherein R is hydrogen or $C_1$-$C_4$ lower alkyl, CN, saturated or unsaturated heterocyclic ring, $C_3$-$C_7$ cycloalkyl ring, phenyl ring optionally substituted by one or more halogens or $C_1$-$C_3$-alkoxy groups;

m is an integer from 1 to 3;
n is zero or an integer from 1 to 2;
p is zero or an integer from 1 to 3.

Also the pharmaceutically acceptable salts as well as the optical antipodes, i.e. the enantiomers, the possible geometric isomers, diastereoisomers and mixtures thereof are included in the scope of the present invention.

The alkyl, alkenyl, alkoxy and alkanoyloxy groups are branched or straight chain groups A halo-$C_1$-$C_6$ alkyl group is preferably trihalo —$C_1$-$C_6$ alkyl, in particular trifluoromethyl.

A halo —$C_1$-$C_4$ alkoxy group is preferably —$OCHF_2$.

A $C_1$-$C_6$ alkyl group is preferably methyl, ethyl, isopropyl or t-butyl.

An aryl group is preferably phenyl.

A $C_3$-$C_5$ alkenyl group is preferably allyl.

A $C_3$-$C_5$ alkynyl group is preferably propargyl.

A $C_3$-$C_7$ cycloaliphatic group is preferably cyclopentyl, cyclohexyl or cycloheptyl.

A monoalkyl amino group is preferably a methyl-, ethyl-, isopropyl- or benzyl-amino group.

A $C_1$-$C_3$ alkoxy is preferably methoxy or isopropoxy.

A $C_1$-$C_3$ alkylthio is preferably methylthio or isopropylthio.

A $C_1$-$C_4$ alkoxycarbonyl is preferably methoxy-, ethoxy- or ter-butoxy-carbonyl group.

When $R_2$ is a five- or six-membered heterocyclic ring, it is preferably pyridyl, furanyl or thienyl.

The non toxic salts, that are pharmaceutically acceptable, include the hydrochlorides, hydrobromides, hydroiodides, (lower)alkylsulfates, (lower)alkyl and aryl sulfonates, phosphates, sulfates, maleates, fumarates, succinates, tartrates, citrates, and others commonly used in the art.

The salts obtained through the variation of the acid used in some cases have special advantage due to increased stability, increased solubility, decreased solubility, ease of crystallization, lack of objectionable taste, etc., but these are all subsidiary to the main physiological action of the free base, which is independent on the character of the acid used in the preparation of the salt.

Specific examples of preferred compounds of the invention are:

a 4-(3-nitrophenyl), (3-chlorophenyl), (3-cyanophenyl), (3-methoxyphenyl), (4-fluorophenyl), (3-methylthiophenyl), (α-benzo[2,3-b]-1,4-dioxan-α-yl), (2-fluoro-5-methylthiophenyl)-2-(2-formylaminoethylthio)methyl-3-ethoxycarbonyl-5-methoxycarbonyl-6-methyl-1,4-dihydropyridine.

a diastereisomer of 2-(2-formylamino-2-phenylethylthio)methyl-3-ethoxycarbonyl-5-methoxycarbonyl-4-(m-nitrophenyl)-6-methyl-1,4-dihydropyridine.

a diastereoisomer of 2-(N-formyl-pyrrolidin-2-yl methylthio)methyl-3-ethoxycarbonyl-5-methoxycarbonyl-4-(m-nitrophenyl)-6-methyl-1.4-dihydropyridine.

2-(2-formylaminoethylthio) methyl-3-ethoxycarbonyl-5-(2-N,N-dimethylamino)ethoxycarbonyl-4-(m-chlorophenyl)-6-methyl-1,4-dihydropyridine.

2-(2-formylaminoethylthio)methyl-3-methoxyethoxycarbonyl-5-methoxycarbonyl-4-(3-methylthiophenyl)-6-methyl-1,4-dihydropyridine.

2-[2-N-(2-cyanoethyl)-N-formylaminoethylthio]methyl-3-ethoxycarbonyl-5-methoxycarbonyl-4-(m-nitrophenyl)-6-methyl-1,4-dihydropyridine.

2-(2-formylaminoethylthio)methyl-3-ethoxycarbonyl-5-(2-N-methyl-N-benzylamino)ethoxycarbonyl-4-(m-nitrophenyl)-6-methyl-1,4-dihydropyridine.

The compounds of the invention are obtained by a process comprising a) forming a thioether bond by reaction of a compound of general formula (II)

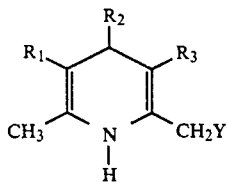
(II)

with a compound of formula III

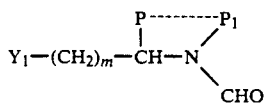
(III)

wherein: $R_1$, $R_2$, $R_3$, m, P, N-$P_1$ are as above defined;
either Y or Y' represents a thiol or a masked thiol group such as thio $C_2$–$C_{12}$ alkanoyl ester or a thiouronium salt $-S-(C=NR_6)NR_7R_8 \; (+)y_2(-)$ the other being a known leaving group such as chlorine, bromine, iodine, trifluoromethane sulphonate, an alkyl- or an arylsulphonate;
$R_6$, $R_7$, $R_8$, which are the same or different, are hydrogen or a $C_1$–$C_4$ alkyl group and $y_2^{(-)}$ is a pharmaceutically acceptable anion;
b) cyclizing a compound of formula IV

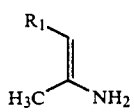
(IV)

with an alkylidene compound of formula V

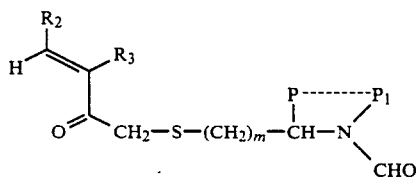
(V)

wherein: $R_1$, $R_2$, $R_3$, P, $NP_1$, m, are as above defined.
c) cyclizing a compound of formula VI

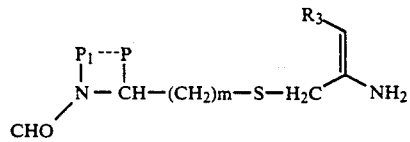
(VI)

with an alkylidene compound of formula VII

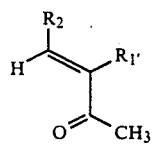
(VII)

wherein $R_2$, $R_3$, P, $NP_1$ and m are as above defined and $R_{1'}$ is preferably $CO_2Ra$, CN, $COCH_3$, $COC_6H_5$.
d) formylating a compound of formula VIII

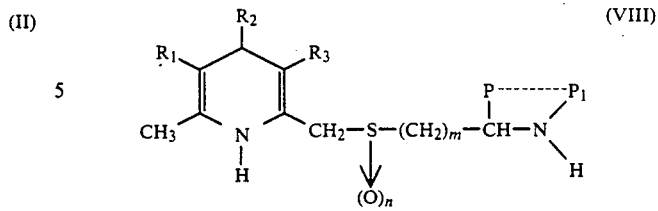
(VIII)

wherein $R_1$, $R_2$, $R_3$, P, $P_1$ and n are as above defined. The above reactions a)-d) give compounds of formula I which may be optionally subjected to further processes such as oxydation, salification, separation of isomers etc.

The thioeterification reaction between a compound of formula II and a compound of formula III may be carried out, as known in the art, using almost equimolar amounts of reagents in an inert solvent at a temperature ranging form $-20°$ to $+60°$ C., in the presence of a base.

Suitable solvents may be chosen in the group of alcohols, amides, linear or cyclic ethers, ketones esters, halogenated hydrocarbon, whereas the base may be an alkali or earth-alkali metal hydroxide, carbonates, bicarbonates, alcoholates, hydrides, amides or organic bases such us triethylamine, pyridine etc.

The selective oxidation of the thioethereal bond of the compounds of formula I where n=0 to give the compounds of formula I wherein n is 1 or 2 is carried out in an inert solvent such as ethyl acetate, ethyl formiate, dichloromethane, 1,2-dichloroethane, chloroform or mixtures thereof, by reaction with one or more molar equivalents of a peracid such as perbenzoic, m-chloroperbenzoic, periodic, monoperftalic, peracetic, performic or peroxytrifluoroacetic acid, working in a temperature ranging from $-30°$ C. to room temperature. Preferably, the reaction is carried out at above 0° C. Compounds of formula I wherein n=1 are obtained using 1 mol. equiv. of peracids, while using 2 or mor mol. equiv. of peracids, compounds with n=2 are obtained.

The cyclization of an enaminoderivative of formula IV and VI with an ethylenederivative of formula V and VII respectively is the well-known Hantzsch reaction, described by F. Brody and P. R. Ruby in "Pyridines and its derivatives", part I, pages 355–533, A. Weissbenger—Interscience, New York 1960.

The formulation reaction of a compound of general formula VIII is also carried out using well-known technique, for instance by treatment in an inert solvent such as dimethyl formamide or dimethyl acetamide, with a 5-10 molar excess of formic acid and heating the mixture for 1 8 h at a temperature ranging from 70° to 120–° C.

Alternatively, an amino compound of formula VIII is reacted in an inert dry solvent such as tetrahydrofuran, benzene, ethylacetate, dimethylformamide or their mixtures with at least a 0.1 molar excess of N-formylimidazole; preferred reaction conditions are from the room temperature to 5° C. for a time from 10 minutes to 1-2 hours.

Alternatively, a salt of a compound of formula VIII (hydrobromide, nitrate, sulphate or emisulphate) is reacted with an excess of formamide at a temperature ranging from 60° to 90° C. for a time from few minutes to 3 hours.

The optical resolution processes are preferably carried out on compounds of formula I wherein n is 0 or 2, whereas chiral compounds wherein n is 1 are preferably obtained by oxidation of the antipodes wherein n is zero.

The optional resolution process is carried out on diastereoisomeric derivatives of compounds I. For examples, diastereoisomeric salts of compounds I with optically pure acids or bases may be prepared by known salification methods and optionally subjected to optical resolution. When Ra contains an amino group, optically pure acids are used while when Ra is hydrogen, optically active bases are used, to give, after the resolution process, optically pure acids of formula I, which may be optionally esterified by known methods. On the other hand, racemic acids of formula I may be esterified with optically pure alcohols and the obtained diastereoisomeric alcohols may optionally be subjected to resolution by crystallization or chromatographic methods. The obtained optically pure esters may be transformed by known methods into acids or esters I.

The compounds of formula II wherein Y is a halogen may be prepared according to a Hantzsch type reaction as in the following scheme described in U.S. Pat. No. 4,839,348 which is hereby incorporated by reference:

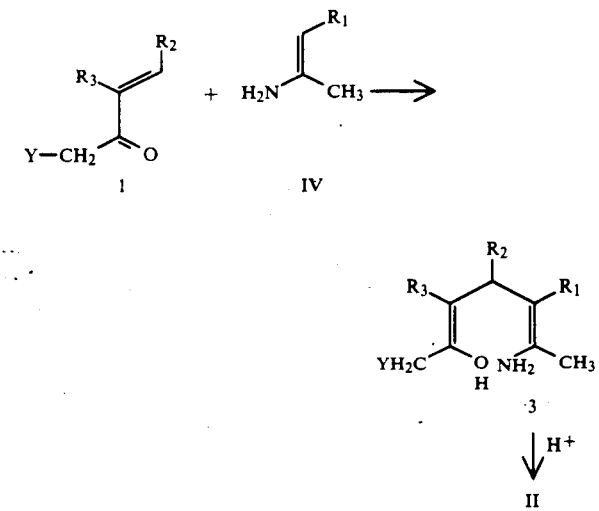

The reaction is carried out under kinetics control conditions by reacting equimolecular compounds of the reagents or in slight excess of the enamino reagent IV, in solvents such as alcohols (methanol, ethanol, isopropanol, n-butanol, isobutanol), benzene, toluene, acetic acid, tetrahydrofuran, pyridine or in mixtures thereof, at temperatures ranging from $+20°$ C. to the solvent boiling temperature, for reaction times from 1 to 48 hours.

Kinetics control conditions are those temperature and time conditions allowing isolation of the product 3 which is then cyclized to compounds II in the presence of acids such as hydrochloric, sulphuric, p-toluenesulfonic acid, at a temperature from $-20°$ C. to $+15°$ C.

The kinetic control is necessary when $R_3$ is a $COOR_4$ group in order to avoid intramolecular cyclization reactions yielding lactone derivatives.

The compounds of general formula II wherein Y is a thiol and/or a masked thiol moiety are prepared by reacting the compounds of formula II wherein Y is a halogen with a thiol of formula $R_4'SH$ wherein $R_4'$ is hydrogen or $C_2$-$C_{12}$ alkanoyl according to per se known methods.

The compounds of formula III, if not already known may be easily prepared from commercialy available compounds, using well-known, safe and unexpensive methods.

A general source of compounds III are aminoalcohols IX

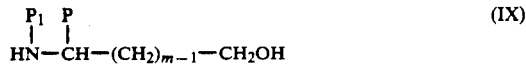

wherein m, P, P1 are as above defined; said alcohols are commercially available or are prepared by reduction of the corresponding amino-carboxy esters or lactames.

Compounds of general formula IX are easily converted into compounds III by known reactions such as formylation and transformation of the alcoholic group into a thiol.

Compounds of general formula V are prepared from compounds of general formula X

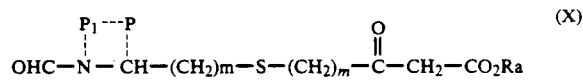

(P, $P_1$, X, m and Ra as above defined) by Knoevenagel condensation with aldehyde of formula XI

($R_2$ as above defined) while compounds of formula VII are prepared from compounds of formula X by reaction with ammonia or ammonium salt.

Compounds of formula X are prepared, for example, via thioetherification reaction of compounds of formula III with 4-chloro-3-oxo-butanoic acid Compounds of general formula IV and XI are known or easily available.

Some formylamino alkyl thiomethyl derivatives of the invention, such as 2-formylamino ethyl thio-4-(m-nitrophenyl)-3-carboethoxy-5-carbomethoxy-6-methyl-1,4-dihydropyridine show peculiar properties such as low oral acute toxicity and high tolerability in some susceptible experimental animals, e.g. dogs, combined with pronounced and long lasting antihypertensive activity at very low doses (for ex. 0.2 mg/kg/os) when tested orally in conscious SH rats once daily.

The antihypertensive effect is dose related in the investigated dose range, for example from 0.05 to 0.8 mg/kg. The maximum hypotensive effect, proportional to the administered dose, takes place 5-7 hours after the administration and the blood pressure is maintained at the decreased level for further 4-5 hours, at least.

The gradual onset of the antihypertensive effect does not seem to be coupled with reflex tachicardia, which is often observed after treatment with other antihypertensive agents such as, for example, hydralazine and many dihydropyridines, in the same experimental models.

On the contrary, no substantial modifications of the mean B.P. and heart rate are observed after one day oral administration of the same compounds to normotensive conscious rats at the same dose range.

After a two weeks treatment consisting of one daily oral administration using a dose range from 0.1 to 0.8 mg/kg, a gradual decrease of mean B.P. also dose-related is observed in the treated conscious SH-rats.

Dosages such as 0.2–0.4 mg/Kg are sufficient to stabilize gradually the mean B.P. to lower level for a 24 hrs period. The drop-out of the pharmacological treatment is not combined with an acute hypertensive rebound effect but in the following 2-3 days the mean blood pressure gradually rises to the initial values.

A similar pharmacological profile is shared by many 2-amino alkyl thio-methyl-1,4-dihydropyridines of formula II. In general they turn out to be effective antihypertensive agents when orally tested in conscious SH rates and well-tolerated in suchronic toxicological studies carried out in male and female normotensive rats, independently from the fact that many of these substances show low $LD_{50}$ in mice by the oral or intraperitoneal route.

Representative results of acute toxicity studies are reported in table 1; the same substances tested orally in conscious SH rats (200–250 g/body weight) show at 1.6 mg/kg a maximum decrease of the mean blood pressure of about 30–80 mmg, with the exclusion of compounds 1, 4, 21, 20, 31 (—BP ranging from 10 to 25 mmHg); 2, 5, 6, 7, 10, 11, 12 (—BP higher than 85 mmHg), whereas the compound 16 d is practically inactive at 3.2 mg/kg.

However, male and female beagle dogs orally treated with 1.5 mg/kg/day (bolus administration) of the compounds 11 and 15 died after three days treatment.

TABLE I

[Structure: 1,4-dihydropyridine with phenyl-X at 4-position, $R_1$ and $R_3$ substituents, CH$_3$ and $CH_2$—S—$(CH_2)_m$—CH—NH with $P_1$—P group]

| | $R_1$ | $R_3$ | X | m | $P_1$------P<br>CH—NH | LD50 in mice mg/kg OS | i.p. |
|---|---|---|---|---|---|---|---|
| 1 | CO$_2$Me | CO$_2$Et | H | 1 | CH$_2$NH$_2$ | 33 | 31 |
| 2 | CO$_2$Me | CO$_2$Et | 2-CF$_3$ | 1 | CH$_2$NH$_2$ | 2 | 2 |
| 3 | CO$_2$Et | CO$_2$Et | 2-CF$_3$ | 1 | CH$_2$NH$_2$ | 9 | 5 |
| 4 | CO$_2$Me | CO$_2$Et | 2-NO$_2$ | 1 | CH$_2$NH$_2$ | 3 | 2 |
| 5 | CO$_2$Et | CO$_2$Et | 2-Cl | 1 | CH$_2$NH$_2$ | 12 | 9 |
| 6 | CO$_2$Me | CO$_2$Et | 2-Cl | 1 | CH$_2$NH$_2$ | 5 | 4 |
| 7 | CO$_2$Me | CO$_2$Et | 3-Cl | 1 | CH$_2$NH$_2$ | 40 | 23 |
| 8 | CO$_2$Me | CO$_2$Et | 2-SCH$_3$ | 1 | CH$_2$NH$_2$ | 8 | 5 |
| 9 | CO$_2$Me | CO$_2$Et | 3-CF$_3$ | 1 | CH$_2$NH$_2$ | 40 | 23 |
| 10 | CO$_2$Et | CO$_2$Et | 3-NO$_2$ | 1 | CH$_2$NH$_2$ | 21 | 20 |
| 11 | CO$_2$Et | CO$_2$Me | 3-NO$_2$ | 1 | CH$_2$NH$_2$ | 52 | 22 |
| 12 | CO$_2$Et | CO$_2$Me | 3-NO$_2$ | 1 | CH$_2$N(CH$_3$)$_2$ | 38 | 25 |
| 13 | CO$_2$Et | CO$_2$Me | 3-NO$_2$ | 1 | CH$_2$NH$_2$ | 21 | 8 |
| 14 | CO$_2$Et | CO$_2$Me | 3-NO$_2$ | 1 | CH$_2$NH—C$_4$H$_9$ | 23 | 12 |
| 15 | CO$_2$Et | CO$_2$Me | 3-NO$_2$ | 1 | CH$_2$NH—C$_4$H$_9$ | 40 | 39 |
| 16a | CO$_2$Et | CO$_2$Me | 3-NO$_2$ | 1 | [pyrrolidine ring structure] | 17 | 7 |
| 16b | | | | | | 39 | 25 |
| 16c | | | | | | 55 | 27 |
| 16d | | | | | | 1000 | 1000 |
| 17 | CO$_2$Et | CO$_2$Me | 3-NO$_2$ | 2 | CH$_2$NH$_2$ | 22 | 16 |
| 18 | CO$_2$Et | CO$_2$Me | 3-NO$_2$ | 3 | CH$_2$NH$_2$ | 11 | 4 |
| 19 | CO$_2$Et | CO$_2$Et | 3-NO$_2$ | 1 | CH$_2$NH—(CH$_2$)$_2$CN | 95 | 54 |
| 20 | CO$_2$Et | CO$_2$Me | 3-NO$_2$ | 1 | CH$_2$NH—(CH$_2$)$_2$CN | 63 | 35 |
| 21 | CO$_2$Et | NO$_2$ | 3-NO$_2$ | 1 | CH$_2$NH$_2$ | 451 | 108 |
| 22 | CO$_2$Et | CN | 3-NO$_2$ | 1 | CH$_2$NH$_2$ | 611 | 82 |
| 23 | CO$_2$CH$_2$CH$_2$<br>\|<br>C$_6$H$_5$CH$_2$N—CH$_3$ | CO$_2$Et | 3-NO$_2$ | 1 | CH$_2$NH$_2$ | 91 | 32 |
| 24 | CO$_2$CH(CH$_3$)$_2$ | CO$_2$Et | 3-NO$_2$ | 1 | CH$_2$NH$_2$ | 53 | 25 |
| 25 | CO$_2$Me | CO$_2$Me | 3-NO$_2$ | 1 | CH$_2$NH$_2$ | 53 | 25 |
| 26 | CO$_2$Me | CO$_2$Et | 3-OCH$_3$ | 1 | CH$_2$NH$_2$ | 82 | 59 |
| 27 | CO$_2$Me | CO$_2$Et | 4-F | 1 | CH$_2$NH$_2$ | 46 | 28 |
| 28 | CO$_2$Me | CO$_2$Et | 3-CN | 1 | CH$_2$NH$_2$ | 34 | 43 |
| 29 | CO$_2$Me | CO$_2$Et | 3-NO$_2$ | 1 | CH(NH$_2$)<br>\|<br>C$_6$H$_5$ | 77 | 46 |
| 30 | CO$_2$Me | CO$_2$Et | 3-NO$_2$ | 1 | CH(NH$_2$)<br>\|<br>CH$_3$ | 42 | 50 |

TABLE I-continued

[Structure: 1,4-dihydropyridine with phenyl-X substituent at 4-position, CH₃ at 2-position, N-H, R₁ and R₃ at 3,5-positions, and CH₂—S—(CH₂)$_m$—CH(NH-P)(P₁) at 6-position]

| | $R_1$ | $R_3$ | X | m | $\overset{P_1------P}{CH-NH}$ | LD50 in mice mg/kg OS | i.p. |
|---|---|---|---|---|---|---|---|
| 31 | CO₂Me | CO₂Et | 3-NO₂ | 1 | CH—NH₂ \| CH₂OH | 371 | 87 |
| 32 | CO₂Et | CO₂Et | 3-NO₂ | 1 | CH—NH₂ \| CO₂Et | 763 | 354 |

Acylation of the amino group of a compound of formula VIII, (for ex. the 2-acetyl amino or 2-benzoylamino derivatives of compounds 11, 15) reduces acute toxicities in mice but in general the long lasting antihypertensive action in SH rats is lost and the compounds require almost two administrations dayly in order to stabilize the mean blood pressure values to lower levels for a 24 hours period. Surprisingly, the 2-formyl amino-alkyl-thio methyl-1,4-dihydropyridines of the present invention do not only show long lasting antihypertensive effect and lower acute toxicities (for ex. 2-formyl-amino-ethyl-thio methyl-4-(m-nitrophenyl)-3-carboethoxy-5-carboethoxy-4-m-nitrophenyl-6-methyl-1,4-dihydropyridine shows LD₅₀ in mice of 200 and 150 mg/kg orally and i.p. respectively) but are well-tolerated in dogs. Male and female beagle dogs orally treated with the latter substance of the invention at dosages as high as 5–12.5 mg/kg/day (bolus administration) do not die after two weeks treatment.

After N-formylation of the side chain amino function of the compound of formula VIII of table I, a 5 to 12 fold acute toxicity reduction in mice is observed. For example, N-formylation of compound 8, increases LD₅₀ in mice (oral) from 8 mg/kg to 90 mg/kg.

Moreover, the ability of the compounds of the invention to inhibit "in vitro" the contractile activity induced by increasing concentration of calcium ions in K⁺-depolarized rat aorta strips was investigated according to the technique of T. Godfraind et al. (Arch. Int. Pharmacodyn. 172, 235, 1968). Representative results of these studies with compound 11 and its N-acetyl and N-formyl derivatives are reported in Table 2.

TABLE II

| 3-ethoxycarbonyl-5-methoxycarbonyl-4-m-nitrophenyl-1,4-dihydropyridines | Inhibition of contractile responses in K⁺ depolarized rat aorta strips by increasing Ca⁺⁺ concentration. IC₅₀ (drug concentration) | |
|---|---|---|
| | after different incubation times | |
| | 2–5 min | 2–3 hrs |
| rac 2-amino-ethyl-thio methyl (as fumarate) | $4.15 \cdot 10^{-7}$ | $9 \cdot 10^{-10}$ |
| (+) antipode | $5 \cdot 10^{-5}$ | $1.1 \cdot 10^{-7}$ |
| (−) antipode | $1.7 \cdot 10^{-7}$ | $2.3 \cdot 10^{-9}$ |
| rac 2-acetylamino ethyl-thio-methyl | $1.1 \cdot 10^{-8}$ | $8.5 \cdot 10^{-9}$ |
| (+) antipode | $2 \cdot 10^{-6}$ | $1.67 \cdot 10^{-7}$ |
| (−) antipode | $4.1 \cdot 10^{-9}$ | $7.49 \cdot 10^{-10}$ |
| rac 2-formylaminoethylthio methyl | $1.62 \cdot 10^{-8}$ | $8.06 \cdot 10^{-10}$ |
| (+) antipode | $10^{-5} \cdot 10^{-6}$ | $5.3 \cdot 10^{-7}$ |
| (−) antipode | $1.07 \cdot 10^{-8}$ | $7 \cdot 10^{-10}$ |
| nifedipine | $2.7 \cdot 10^{-8}$ | $2.7 \cdot 10^{-8}$ |

The reported results further confirm that better inhibiting activities (ID₅₀ ranging from $10^{-7}$ to $10^{-10}$) may be observed after longer incubation times with the investigated tissue preparations than after shorter ones (ID₅₀ ranging from $10^{-5}$ to $10^{-9}$) whereas the behaviour of the standard compound nifedipine is not related to the incubation time.

The shorter lasting antihypertensive effect of the N-acetyl compound and the long lasting effects of the compounds 11 and of its N-formyl derivative does not seem to be correlated with "in vitro" experimental results related to the supposed Ca-antagonist potency and capability of relaxing smooth muscles, phenomenon which cannot be easily explained on the basis of the present knowledge.

Independently from this aspect, the particular antihypertensive effect, its gradual onset, the long lasting action combined with lower acute toxicity and with increased tolerability in dogs provide evidence that the compounds of the invention are useful in human and veterinary therapy for the treatment of hypertensive situations of different origin, and for the treatment and prevention of cardiovascular and coronary diseases.

In order to attain the desired effects in human and veterinary therapy, the compounds of the invention may be administered parenterally, for example by intravenous, hypodermic or intramuscular injection, by infusion, rectally or orally. The compounds may also be administered in pure form or in the form of a pharmaceutical composition.

The formulation of suitable pharmaceutical compositions may be prepared according to techniques well-known in the art, such as the ones described in "Remington's Pharmaceutical Sciences Handbook", Hack Publishing Co., U.S.A.

When the compounds of the invention are used as antihypertensive drugs, the dosage will vary according to the seriousness of the hypertension and to the administration route.

The amount of the active principle administered may vary, anyhow, between 1 mcg/kg/die and 1 mg/kg/die, preferably between 5 mcg/die and 0.1 mg/kg/die, by the oral route and from 0.1 mcg/kg/die to 0.5 mg/kg/die, preferably from 0.5 mcg/kg/die to 0.2 mg/kg/die, by the parenteral route.

A dosage for oral administration may contain, for example, between 50 mcg to 10 mg of active principle.

The compounds of the invention may be administered even once a day, however more spaced and/or repeated administrations may be, at least in some cases, more suitable and may vary according to the conditions of the patient and to the administration route or to the dosage.

By oral administration the compound may be formulated in solid or liquid preparations, such as capsules, pills, tablets, powders, solutions, suspensions or emulsions.

By parenteral administration the compound may be administered in injectable formulations, dissolved or suspended in physiologically acceptable diluents, with a vehicle that may be a sterile liquid such as water or an oil, with or without the addition of other excipients.

The compounds may also be administered per rectal route, in the form of suppositories, mixed with the conventional vehicles.

The preferred administration route of the compounds of the invention is the oral route.

The invention is illustrated by the following non limitative examples, wherein the abbreviations EtOH, DME, THF, $Et_2O$, AcOEt, AcOH refer to ethanol, dimethoxyethane, methanol, tetrahydrofuran, ethyl ether, ethyl acetate, acetic acid respectively.

PREPARATION 1

A stirred solution of cysteamine hydrochloride (g 20) in formamide (ml 20) in heated at 75°–80° C. for 2 hours. After cooling at room temperature, the $NH_4Cl$ precipitate is filtered off and washed with a little formamide. The solution of N-formyl cysteamine (about 18 g) in formamide is then diluted with EtOH (160 ml), cooled at 0° C., and in nitrogen atmosphere is treated under stirring with 20% aqueous NaOH (170 ml) and with a solution of ethyl 4-chloro-3-oxo-butanoate (28,4 g) in EtOH (20 ml). After 30 minutes the mixture is poured into water (2000 ml) and extracted with AcOEt (3×200 ml). The combined extracts are washed with a saturated solution of $NaH_2PO_4$ (3×50 ml) $H_2O$ (3×100 ml), dried on $Na_2SO_4$ and evaporated to dryness in vacuum to give 40.5 g of ethyl 4-(2-formylaminoethylthio)-3-oxo-butanoate as an oil;

1H-NMR ($CDCl_3$), δ(TMS): 1.10–1.30 (3H, t); 2.20–2.60 (4H, m); 3.40–4.10 (6H, m); 6.60 (1H, m); 8.10 (1H, S).

Using, in the same procedure, the methyl and the methoxyethyl 4-chloro-3-oxobutanoates, the corresponding methyl and methoxyethyl 4-(2-formylaminoethylthio)-3-oxo-butanoates are prepared.

PREPARATION 2

Acetic acid is added to a solution of ethyl 4-(2-formylamino-ethylthio)-3-oxo-butanoate (12.5 g) in MeOH (ml 120), previously saturated with ammonia at 0° C. and cooled at 0° C., up to pH 4–45. The mixture is refluxed for 2 hours and the excess solvent is evaporated in vacuum, to give a syrup from which a solid material is separated by treatment with AcOEt. After filtration, the organic phase is washed with water (8×10 ml), and with a saturated aqueous solution of $NaHCO_3$ (3×10 ml), dried ($Na_2SO_4$) and concentrated in vacuum to give 11,5 g of ethyl 3-amino-4-(2-formylaminoethylthio)crotonate as a yellow oil.

1H-NMR: ($CDCl_3$), δ(TMS): 1.10–1.20(3H,t); 2.20–2.60 (4H, m); 3.80–4.10 (4H, m); 5.20–5.40 (2H, m); 5.70 (1H, m); 6.60 (1H, m); 8.10 (1H, s). Methyl and methoxiethyl 3-amino-4-(2-formylaminoethylthio) crotonate are likewise prepared.

PREPARATION 3

A solution of 3-chlorobenzaldehyde (10 g), ethyl 4-(2-formylaminoethylthio)-3-oxo-butanoate (16,7 g), AcOH (2 ml) and piperidine (0,6 ml) in benzene (120 ml) is refluxed in a Dean-Stark apparatus for 6 hours. After cooling at room temperature, the mixture is washed with $H_2O$ (3×20 ml), with a saturated solution of $NaHCO_3$ (3×10 ml), with a solution of $H_2SO_4$ (2N, 3×10 ml) and again with $H_2O$ (3×30 ml). The organic phase is dried ($Na_2SO_4$) and concentrated in vacuum to give 16 g of ethyl 2-Z, E-(3-chlorophenylmethylene)-4-(2-formylaminoethylthio)-3-oxo-butanoate, as an oil.

1H-NMR($CDCl_3$), δ(TMS), 1.1–1.2 (3H, t); 2.2–2.4 (2H,t); 2.7–3.0 (2H, m); 8.9–4.2 (4H, m); 6.8–7.9 (7H, m).

EXAMPLE 1

A solution of ethyl 3-amino-4-(2-formylamino ethylthio) crotonate (5.3 g) and 3-Z, E-(m-nitrophenylmethylene)-2,4-pentanedione (4.9 g; from Knoevenagel condensation of 3-nitrobenzaldehyde with 2,4-pentanedione) in EtOH (100 ml) is refluxed for 4 hours, it is cooled at 0° C. and acidified (pH 1:2) with few drops of EtOH saturated with gaseous HCl. After 15 minutes the solvent is evaporated at reduced pressure, the residue dissolved in AcOEt (80 ml), washed with a saturated solution of $NaHCO_3$ (3×15 ml), with water (3×30 ml), dried ($Na_2SO_4$) and concentrated. The residue is purified by chromatography on $SiO_2$ (300 g, eluent AcOEt/MeOH 80/20) to give 4.9 g of 2-(2-formylaminoethylthio) methyl-3-ethoxycarbonyl-4-(m-nitrophenyl)5-acetyl-6-methyl-1,4-dihydropyridine, m.p. 140°–142° C. (EtOH).

EXAMPLE 2

A solution of ethyl 3-amino-4-(2-formylaminoethylthio) crotonate (1 g) and methyl 2-Z,E-(2-nitro-5-methylthiophenylmethylene)-3-oxobutanoate (0,95 g, m.p. 69-7, obtained by Knoevenagel condensation of methyl acetoacetate and 2-nitro-5-methylthiobenzaldehyde), in EtOH (ml 10) is refluxed for 24 hours, then it is evaporated to dryness. The residue is dissolved in $Et_2O$ (ml 30), washed with HCl (2N, 3×5 ml), $H_2O$ (3×10 ml), dried and concentrated in vacuum. After column chromatography on $SiO_2$ 30 g, eluent $Et_2O$/AcOEt 60/40) 1.1 g of 2-(2-formylamino ethylthio)methyl-3-ethoxycarbonyl-5-methoxycarbonyl-4-(2-nitro-5-methylthiophenyl)-6-methyl-1,4-dihydropyridine, m.p. 148°–150° ($Et_2O$) are obtained.

Using the procedure of example 1 or 2 the following compounds are prepared:
2-(2-formylaminoethylthio)methyl-3-ethoxycarbonyl-5-methoxycarbonyl-4-(2, 3-dichlorophenyl)-6-methyl-1,4-dihydropyridine, m.p. 122°–124° C.

2-(2-formylaminoethylthio)methyl-3-ethoxycarbonyl-5-cyano-4-phenyl-6-methyl-1,4-dihydropyridine 2-(2-formylaminoethylthio)methyl-3-ethoxycarbonyl-5-cyano-4-(3-methoxyphenyl)-6-methyl-1,4-dihydropyridine 2-(2-formylaminoethylthio)methyl-3-ethoxycarbonyl-5-benzoyl-4-phenyl-6-methyl-1,4-dihydropyridine 2-(2-formylaminoethylthio)methyl-3-methoxycarbonyl-5-methoxycarbonyl-4-(2-fluoro-3-methythio-phenyl)-6-methyl-1,4-dihydropyridine 2-(2-formylaminoethylthio)methyl-3-methoxycarbonyl-5-methoxycarbonyl-4-(2-methylthiophenyl)-6-methyl-1,4-dihydropyridine.

EXAMPLE 3

A solution of ethyl 3-amino-4-(2-formyl-aminoethyl-thio)crotonate (7 g) and methyl 2-E,Z-(3-nitro-phenyl-methylen)-3-oxobutanoate (6 g) in ETOH (70 ml) is refluxed for 18 hours, then it is concentrated in vacuum. The residue is dissolved in AcOEt (100 ml), washed with HCl (2N, 3×30 ml), H$_2$O (3×50 ml), dried on Na$_2$SO$_4$, concentrated in vacuum and purified by column chromatography on SiO$_2$ (300 g, eluent AcOEt-hexane 90/10), obtaining 8 g of 2-(2-formylaminoethyl-thio)-methyl-3-ethoxycarbonyl-5-methoxycarbonyl-4-(m-nitrophenyl)-6-methyl-1.4-dihydropyridine, mp. 109°–11° C.

EXAMPLE 4

A solution of ethyl 2-Z,E-(3-chlorophenylmethylene)-4-(2-formylaminoethylthio)-3-oxo-butanoate (4 g) and methyl 3-aminocrotonate (1.2 g) in EtOH (40 ml) is refluxed for 3 hours, the mixture cooled at room temperature acidified to pH 1:2 with a few drops of EtOH saturated with gaseous HCl and, after 20 minutes, evaporated to dryness; a solution of the residue in AcOEt (60 ml) is washed with a saturated solution of NaHCO$_3$ (3×10 ml), H$_2$O (3×20 ml), dried (Na$_2$SO$_4$) and concentrated in vacuum. After chromatography on silica gel (150 g; eluent: AcOEt) 4.3 g of 2-(2-formylaminoethylthio)methyl-3-ethoxycarbonyl-4-(3-chlorophenyl)-5-methoxycarbonyl-6-methyl-1.4-dhydropyridina are obtained as a foam.

$^1$H-NMR (CDCl$_3$): δ(TMS)=1.10–1.25 (3H, t); 2.20–2.80: (5H, m); 3.20–3.70 (5H, m); 3.80–4.20: (4H, m); 5.00 (1H, s); 6.50 (1H, m); 7.00–7.20: (5H, m); 8.10 (1H, s).

Using the above described procedure, the following compounds are prepared 2-(2-formylaminoethylthio)methyl-3-ethoxycarbonyl-5-cyano-4-(m-chlorophenyl)-6-methyl-1.4-dihydropyridine 2-(2-formylaminoethylthio)methyl-3-ethoxycarbonyl-5-(2-N,N-dimethylamino)ethoxycarbonyl-4-(m-chlorophenyl)-6-methyl-1.4-dihydropyridine 2-(2-formylaminoethylthio)methyl-3-ethoxycarbonyl-5-isopropoxycarbonyl-4-(m-chlorophenyl)-6-methyl-1.4-dihydropyridine 2-(2-formylaminoethylthio)methyl-3-ethoxycarbonyl-5-t-butoxycarbonyl-4-(m-chlorophenyl)-6-methyl-1.4-dihydropyridine 2-(2-formylaminoethylthio)methyl-3-ethoxycarbonyl-5-methoxycarbonyl-4-(m-nitrophenyl)-6-methyl-1.14-dihydropyridine, mp. 109°–11° C.

EXAMPLE 5

In nitrogen atmosphere, a stirred mixture of 2-mer captomethyl-3-ethoxycarbonyl-5-methoxycarbonyl-4-(m-nitrophenyl)-6-methyl-1.4-dihydropyridine (5 g), K$_2$CO$_3$ (2 g) and (S)-2-formylamino-2-phenyl-ethanolmethanesulfonate (3 g from S(+)-N-formyl-phenylglycin) in DMAF (50 ml) is heated for 12 hours at 50° C. The cooled mixture is poured in ice-water (500 ml) and extracted with AcOEt (30 ml×3). After usual work-up, the combined organic extracted are evaporated to dryness, to give a diasteroisomer mixture of 4(S)2'(S) and 4(R)2'(S)-2-(2'-formylamino-2'-phenylethylthio)methyl-3-ethoxycarbonyl-5-methoxycarbonyl-4-(m-nitrophenyl)-6-methyl-1.4-dihydropyridine, which are separated by HPL-chromatography on SiO$_2$ (eluent AcOEt/hexane). The more polar diastereoisomer (1.7 g) is a foam, the less polar is obtained as crystalline compound (2.2 g, m.p. 66°–70° C., C$_{27}$H$_{29}$N$_3$O$_7$S.2-/$_3$Et$_2$O).

Using the above described procedure the following compounds are prepared:

2-(2-formylamino-3-phenylpropylthio)methyl-3-ethoxycarbonyl-5-methoxycarbonyl-4-(m-nitrophenyl)-6-methyl-1.4-dihydropyridine;

2-(2-formylaminopropylthio)methyl-3.5-di-ethoxycarbonyl-4-(m-trifluoromethylphenyl)-6-methyl-1.4-dihydropyridine;

2-/2-formylamino-3-(4-imidazolyl)propylthio/methyl-3-methoxycarbonyl-5-isopropoxycarbonyl-4-(m-cyanophenyl)-6-methyl-1.4-dihydropyridine 2'-R-2-(2'-formylamino-2'-phenylethylthio)methyl-3-ethoxycarbonyl-5-methoxycarbonyl-4-(m-nitrophenyl)-6-methyl-1.4-dihydropyridine 2-(2-formylaminoethylthio)methyl-3-ethoxycarbonyl-5-methoxycarbonyl-4-(m-nitrophenyl-6-methyl-1.4-dihydropyridine, m.p. 109°–111° C.

EXAMPLE 6

A solution of 2-chloromethyl-3-ethoxycarbonyl-4-(o-methylthiophenyl)-5-methoxycarbonyl-6-methyl-1.4-dihydro pyridine (2.1 g) in EtOH (10 ml) is added dropwise at 0° C. to a solution of N-n-butyl-N-(2-acetylthio-ethyl)formamide (1.2 g) and NaOH (20% water solution, 1.2 g). After 3 hours at 0° C., the reaction mixture is warmed at room temperature and stirred for 30 minutes, then it is concentrated in vacuum. After usual work-up, and column chromatography on SiO$_2$ (80 g; eluent AcOEt/Et$_2$O 70/90) 1.8 g of 2-/2-N-formyl-N-butylamino)ethylthio/methyl-3-ethoxycarbonyl-4-(o-methylthiophenyl)-5-methoxycarbonyl-6-methyl-1.4-dihydropyridine are obtained as a foam.

$^1$H-NMR (CDCl$_3$): δ(TMS) 0.1–1.3 (6H, m): 1.5–2.0 (4H, m; 2.1–3.0 (10H, m); 3.20–4.20 (8H, m); 5.10 (1H, s); 6.8 (1H, m); 6.9–7.4 (6H, m); 8.1 (1H, s)

Using the above described procedure the following compounds are prepared:

2-[(N-formyl-pyrrolidin-2-yl)methyl-thio]methyl-3-ethoxycarbonyl-5-methoxycarbonyl-4-(m-nitrophenyl)-6-methyl-1,4-dihydropyridine;

2-(2-formylaminoethylthio)methyl-3-ethoxycarbonyl-5-methoxycarbonyl-4-(2-chlorophenyl)-6-methyl-1,4-dihydropyridine;

2-(2-formylaminoethylthio)methyl-3-ethoxycarbonyl-5-methoxycarbonyl-4-(2-trifluoromethylphenyl)-6-methyl-1,4-dihydropyridine;

2-(2-formylaminoethylthio)methyl-3-ethoxycarbonyl-5-methoxycarbonyl-4-(3-cyanophenyl)-6-methyl-1,4-dihydropyridine;

2-(2-formylaminoethylthio)-3-ethoxycarbonyl-5-methoxycarbonyl-4-(3-methoxyphenyl)-6-methyl-1,4-dihydropyridine;

2-(2-formylaminoethylthio)methyl-3-ethoxycarbonyl-5-methoxycarbonyl-4-phenyl-6-methyl-1,4-dihydropyridine;

2-(2-formylaminoethylthio)methyl-3-ethoxycarbonyl-5-methoxycarbonyl-4-(p-fluorophenyl)-6-methyl-1,4-dihydropyridine;

2-(2-formylaminoethylthio)methyl-3-ethoxycarbonyl-5-methoxycarbonyl-4-(2-trifluoromethylphenyl)-6-methyl-1,4-dihydropyridine;

2-(2-formylaminoethylthio)methyl-3,5-di-ethoxycarbonyl-4-(3-pyridyl)-6-methyl-1,4-dihydropyridine;

2-(4-formylaminoethylthio)methyl-3,5-diethoxycarbonyl-4-(m-chlorophenyl)-6-methyl-1,4-dihydropyridine;

2-(2-formylaminoethylthio)methyl-3-ethoxycarbonyl-5-methoxycarbonyl-4-(m-nitrophenyl)-6-methyl-1,4-dihydropyridine, mp 109°–111° C.

2-(2-formylaminoethylthio)methyl-3-ethoxycarbonyl-4-/benzo-(2,3-b)-1,4-dioxan-α-yl/-5-methoxycarbonyl-6-methyl-1,4-dihydropyridine;

2-(2-formylaminoethylthio)methyl-3-ethoxycarbonyl-5-(2-N-methyl-N-benzylamino)ethoxycarbonyl-4-(m-nitrophenyl)-6-methyl-1,4-dihydropyridine.

EXAMPLE 7

A solution of 2-(2-aminoethylthio)methyl-3-ethoxycarbonyl-5-methoxycarbonyl-4-(2-chlorophenyl)-6-methyl-1,4-dihydropyridine (4.4 g) in THF (44 ml) is added to a stirred solution of N-formylimidazole, "in situ" prepared from formic acid (0.6 ml) and N,N-carbonyldiimidazole (2.5 g), at 0° C., in THF (25 ml).

After 30 minutes the reaction mixture is poured into ice/water (2/1; 500 ml), extracted with AcOEt (3×50 ml), the combined extracts washed with a saturated solution of NaH$_2$PO$_4$ (3×10 ml), a saturated solution of NaHCO$_3$ (3×10 ml), and then with H$_2$O (3×50 ml), dried (Na$_2$SO$_4$) and concentrated under vacuum.

3.7 g of 2-(2-formylaminoethylthio)methyl-3-ethoxycarbonyl-5-carbomethoxy-4-(2-chloro)-6-methyl-1,4-dihydropyridine are obtained from Et$_2$O.

EXAMPLE 8

A solution of 2-[2-[N-(2-cyanoethyl)aminoethyl]thio]methyl-3-ethoxycarbonyl-5-methoxycarbonyl-4-(m-nitrophenyl)-6-methyl-1,4-dihydropyridine (5.8 g) in N,N-dimethylformamide (100 ml) and formic acid (100 ml) is heated at 100° C. for 6 hours, then poured in ice/water (500 ml) extracted with Et$_2$O(3×50 ml); the combined organic extracts are washed with a saturated solution of NaHCO$_3$ (3×30 ml), H$_2$O (3×20 ml), dried (Na$_2$SO$_4$) and evaporated to dryness. The residue is crystallized from EtOH to give 4.15 g of 2-[2-N-(2-cyanoethyl)-N-formylaminoethylthio]methyl-3-ethoxycarbonyl-5-methoxycarbonyl-4-(m-nitrophenyl)-6-methyl-1,4-dihydropyridine, mp 110°–112° C.

Using the above described procedure, the following compounds are prepared.

2-(2-formylamino-2-ethoxycarbonylethylthio)methyl-3,5-diethoxycarbonyl-4-(m-nitrophenyl)-6-methyl-1,4-dihydropyridine 2-(2-formylaminoethylthio)methyl-3-ethoxycarbonyl-5-nitro-4-(m-nitrophenyl)-6-methyl-1,4-dihydropyridine.

EXAMPLE 9

A solution of m-chloroperbenzoic acid (1.3 g, 1 equiv. mol) in 1,2-dichloroethane (15 ml) is added at −10° C. to a solution of 2-(2-formylaminoethylthio)-methyl-3-ethoxycarbonyl-5-methoxycarbonyl-4-(m-nitro-phenyl)-6-methyl-1,4-dihydropyridine (3.5 g) in 1,2-dichloroethane (30 ml).

After 30 minutes the solution is filtered, washed with Na$_2$S$_2$O$_3$ (5% water solution, 3×5 ml), NaHCO$_3$ (saturated water solution, 3×10 ml), H$_2$O (3×10 ml), dried (Na$_2$SO$_4$) and evaporated in vacuum to give 3.4 g of 2-(2-formylaminoethylsulfinyl)methyl-3-ethoxycarbonyl-5-methoxycarbonyl-4-(m-nitrophenyl)-6-methyl-1,4-dihydropyridine as a foam.

1H-NMR (CDCl$_3$ δ(TMS): 1.00–1.2 (3H, t); 2.1 (3H, t); 2.80–3.70 (4H, m); 3.90–4.30 (4H, m); 5.10 (1H, m); 6.50 (1H, m); 7.10–8.20 (6H, m).

Using the above described procedure the following 2-(2-formylaminoethylsulfinyl)-6-methyl-1,4-dihydropyridines are prepared:

3-ethoxycarbonyl-5-cyano-4-(m-nitrophenyl);
3-ethoxycarbonyl-5-cyano-4-(m-chlorophenyl);
3,5-diethoxycarbonyl-4-(m-methylthiophenyl);
3,5-dimethoxycarbonyl-4-(m-trifluoromethylphenyl).

EXAMPLE 10

A solution of m-chloroperbenzoic acid (3.8 g, equiv. mol) in MeOH (30 ml) is added at 10° C. to a solution of 2-(2-aminoethylthio)methyl-3-ethoxycarbonyl-5-methoxycarbonyl-4-(m-nitrophenyl)-6-methyl-1,4-dihydropyridine (5 g) in MeOH (100 ml), the mixture is then warmed at 15°–20° C. and stirred for 30 minutes. The solvent is then evaporated at reduced pressure, the residue partitioned between CH$_2$Cl$_2$ (80 ml) and H$_2$O (30 ml), the organic phase is washed with sodium thiosulfate (5% water solution) and then worked-up as described in example 8 to give 4.8 g of 2-(2-aminoethylsulfonyl)methyl-3-ethoxycarbonyl-5-methoxycarbonyl-4-(m-nitrophenyl)-6-methyl-1,4-dihydropyridine as an amorphous solid.

1H-NMR (CDCl$_3$) δ(TMS) 1.0–1.2 (3H, t); 2.1 (3H, t); 3.0–3.7 (4H, m), 4.10–4.30 (4H, m); 5.1 (1H, m); 6.8 (1H, m) 7.10–8.20 (6H, m).

Using the above described procedure the following compounds are prepared:

2-(2-formylaminoethylsulfonyl)-6-methyl-1,4-dihydropyridines:

3,5-diethoxycarbonyl-4-(m-methylthiophenyl)-3-ethoxycarbonyl-5-methoxyethoxycarbonyl-4-(m-chlorophenyl).

EXAMPLE 11

Fractional crystallization of the (±)2-(2-ammoniummethylthio)methyl-3-ethoxycarbonyl-5-methoxycarbonyl-4-(m-nitrophenyl)-6-methyl-1,4-dihydropyridine salt with (+) and (−)camphor-10-sulfonic acids from EtOH produces 2 optical isomers: (+)free base [α]$_D$=+1.8 (MeOH c=10%) as (+)emifumarate salt m.p. 105°–107° C., [α]$_D$=+3.6 (MeOH c=9.7%) and (−)free base, [α]$_D$=−1.7 (MeOH c=19.8%), as emifumarate salt m.p. 106°–108° C., [α]$_D$=3.4 (MeOH c=9.4%).

Starting from the pure enantiomers, as free bases, using the procedures described in examples 7, 8, the enantiomeric 2-(2-formylaminomethylthio)methyl-3-ethoxycarbonyl-5-methoxycarbonyl-4-(m-nitrophenyl)-6-methyl-1,4-di-hydropyridines are obtained as amorphous solids.

(+)N-formylamino isomer: C$_{21}$H$_{35}$N$_3$O$_7$S. ½ H$_2$O

[α]$_D$=+13.6, [α]$_{546}$=+22.2 (MeOH, c=2.14)

(−)N-formylamino isomer: $C_{21}H_{35}N_3O_7S \cdot \frac{1}{2} H_2O$ $[\alpha]_D = -13.7$, $[\alpha]_{546} = -22.3$ (MeOH, c=2.07)

We claim:

1. Compounds of formula I

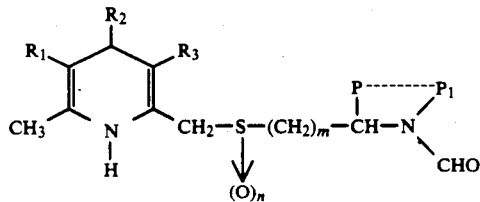

wherein:

R$_1$ represents:
- a COCH$_3$, COC$_6$H$_5$, CN or NO$_2$ group;
- a COORa group, wherein Ra represent hydrogen, C$_1$–C$_6$ straight or branched alkyl, optionally bearing at least one substituent selected from the group consisting of C$_1$–C$_6$ alkoxy groups and secondary amino groups of formula —NR$_4$R$_5$ wherein R$_4$ and R$_5$, that may be the same or different, represent C$_1$–C$_6$ alkyl, phenyl, benzyl or, taken together with the nitrogen atom, form a five or six membered ring;

R$_2$ is a phenyl ring unsubstituted or substituted with at least one substituent selected from the group consisting of C$_1$–C$_6$ alkyl, halogen, nitro, cyano, C$_1$–C$_6$ alkoxycarbonyl, C$_1$–C$_6$ alkylthio, C$_1$–C$_6$ alkylsulfinyl; pentafluorophenyl; α- or β-naphthyl; a five- or six-membered heterocyclic ring; α-benzo (2,3-b)-1,4-dioxan-α-yl; α-benzofuroxanyl;

R$_3$ represents a COORa group wherein Ra is as above defined;

P is selected from the group consisting of hydrogen, —(CH$_2$)$_p$—W and C$_1$–C$_8$ linear or branched alkyl;

N-P$_1$ is the residue of a primary or secondary amino group wherein P$_1$ is selected from the group consisting of hydrogen, C$_1$–C$_6$ lower linear or branched alkyl group and —(CH$_2$)$_p$—W;

P, taken together with P$_1$ and the nitrogen atom to which P$_1$ is linked, may form a pyrrolidine or a piperidine ring;

W is selected from the group consisting of hydroxymethyl, formyloxymethyl, CO$_2$R wherein R is hydrogen or C$_1$–C$_4$ lower alkyl, CN, 4-imidazolyl, C$_3$–C$_7$ cycloalkyl ring, phenyl ring optionally constituted by at least one substituent selected from the group consisting of halogens and C$_1$–C$_3$-alkoxy groups;

m is an integer from 1 to 3;

n is zero or an integer from 1 to 2;

p is zero or an integer from 1 to 3, their salts, enantiomers, diastereoisomers or mixtures thereof.

2. Compounds according to claim 1 wherein R$_1$ represents a COCH$_3$, COC$_6$H$_5$, CN or NO$_2$ group.

3. Compounds according to claim 1 wherein R$_1$ represents a COORa group, wherein Ra is as above defined.

4. Compounds according to any one of claims 1, 2, or 3 wherein R$_2$ is a phenyl ring unsubstituted or substituted with one or more C$_1$–C$_6$ alkoxy carbonyl, C$_1$–C$_6$ alkylthio, C$_1$–C$_6$ alkylsulfinyl.

5. A compound according to claim 1 selected from the group consisting of:
- 4-(3-nitrophenyl)-2-(2-formylaminoethylthio)methyl-3-ethoxycarbonyl-5-methoxycarbonyl-6-methyl-1,4-dihydropyridine;
- 4-(3-chlorophenyl)-2-(2-formylaminoethylthio)methyl-3-ethoxycarbonyl-5-methoxycarbonyl-6-methyl-1,4-dihydropyridine;
- 4-(3-cyanophenyl)-2-(2-formylaminoethylthio)methyl-3-ethoxycarbonyl-5-methoxycarbonyl-6-methyl-1,4-dihydropyridine;
- 4-(3-methoxyphenyl)-2-(2-formylaminoethylthio)-methyl-3-ethoxycarbonyl-5-methoxycarbonyl-6-methyl-1,4-dihydropyridine;
- 4-(4-fluorophenyl)-2-(2-formylaminoethylthio)methyl-3-ethoxycarbonyl-5-methoxycarbonyl-6-methyl-1,4-dihydropyridine;
- 4-(3-methylthiophenyl)-2-(2-formylaminoethylthio)-methyl-3-ethoxycarbonyl-5-methoxycarbonyl-6-methyl-1,4-dihydropyridine;
- 4-(α-benzo[2,3-b]-1,4-dioxan-α-yl)-2-(2-formylaminoethylthio)methyl-3-ethoxycarbonyl-5-methoxycarbonyl-6-methyl-1,4-dihydropyridine;
- 4-(2-fluoro-5-methylthiophenyl)-2-(2-formylaminoethylthio)methyl-3-ethoxycarbonyl-5-methoxycarbonyl-6-methyl-1,4-dihydropyridine;
- 2-(2-formylaminoethylthio)methyl-3-ethoxycarbonyl-5-(2-N,N-dimethylamino)ethoxycarbonyl-4-(m-chlorophenyl)-6-methyl-1,4-dihydropyridine;
- 2-(2-formylaminoethylthio)methyl-3-methoxyethoxycarbonyl-5-methoxycarbonyl-4-(3-methylthiophenyl)-6-methyl-1,4-dihydropyridine;
- 2-[2-N-(2-cyanoethyl)-N-formylaminoethylthio]-methyl-3-ethoxycarbonyl-5-methoxycarbonyl-4-(m-nitrophenyl)-6-methyl-1,4-dihydropyridine; and
- 2-(2-formylaminoethylthio)methyl-3-ethoxycarbonyl-5-(2-N-methyl-N-benzylamino)ethoxycarbonyl-4-(m-nitrophenyl)-6-methyl-1,4-dihydropyridine.

6. A diastereoisomer selected from the group consisting of:
(1) diastereoisomers of 2-(2-formylamino-2-phenylethylthio)methyl-3-ethoxycarbonyl-5-methoxycarbonyl-4-(m-nitrophenyl)-6-methyl-1,4-dihydropyridine;
(2) diastereoisomers of 2-(N-formyl-pyrrolidin-2-yl methylthio)methyl-3-ethoxycarbonyl-5-methoxycarbonyl-4-(m-nitrophenyl)-6-methyl-1,4-dihydropyridine.

7. A compound according to claim 1, which is the levorotatory enantiomer;
(−) 2-(2-formylaminomethylthio)methyl-3-ethoxycarbonyl-5-methoxycarbonyl-4-(m-nitrophenyl)-6-methyl-1,4-dihydropyridine.

8. The compound:
4-(3-nitrophenyl)-2-(2-formyl aminoethylthio)methyl-3-ethoxy carbonyl-5-methoxycarbonyl-6-methyl-1,4-dihydropyridine.

9. A pharmaceutical composition containing, an effective amount of a compound of any one of claims 1, 2, 3 and 5 in admixture with a pharmaceutically acceptable excipient.

10. A pharmaceutical composition containing, an effective amount of a compound of claim 4 in admixture with a pharmaceutically acceptable excipient.

* * * * *